(12) United States Patent
Dolek

(10) Patent No.: US 12,086,683 B2
(45) Date of Patent: Sep. 10, 2024

(54) CYCLE COUNTER MECHANISM FOR USE IN AN AUTOCLAVE OVEN

(71) Applicant: TUSAS-TURK HAVACILIK VE UZAY SANAYII ANONIM SIRKETI, Ankara (TR)

(72) Inventor: Turker Dolek, Ankara (TR)

(73) Assignee: TUSAS-TURK HAVACILIK VE UZAY SANAYII AS, Ankara (TR)

( * ) Notice: Subject to any disclaimer, the term of this patent is extended or adjusted under 35 U.S.C. 154(b) by 0 days.

(21) Appl. No.: 17/927,060

(22) PCT Filed: Mar. 29, 2021

(86) PCT No.: PCT/TR2021/050276
§ 371 (c)(1),
(2) Date: Nov. 22, 2022

(87) PCT Pub. No.: WO2021/242200
PCT Pub. Date: Dec. 2, 2021

(65) Prior Publication Data
US 2023/0289555 A1    Sep. 14, 2023

(30) Foreign Application Priority Data

May 29, 2020    (TR) .................................. 2020/08311

(51) Int. Cl.
*G06M 1/08*    (2006.01)
*A61B 90/00*    (2016.01)
*G06M 1/18*    (2006.01)

(52) U.S. Cl.
CPC ............. *G06M 1/083* (2013.01); *G06M 1/18* (2013.01); *A61B 2090/0803* (2016.02)

(58) Field of Classification Search
None
See application file for complete search history.

(56) References Cited

U.S. PATENT DOCUMENTS 5,452,335 A     9/1995   Slater et al.
6,629,499 B1   10/2003   Greene et al.

FOREIGN PATENT DOCUMENTS

EP           0581400 A1    2/1994
IT     201800006509 A1   12/2019

OTHER PUBLICATIONS

International Search Report and Written Opinion for PCT application No. PCT/TR2021/050276, mailed Jul. 13, 2021.

(Continued)

*Primary Examiner* — Suezu Ellis
(74) *Attorney, Agent, or Firm* — Notaro, Michalos & Zaccaria P.C.

(57) ABSTRACT

A cycle counter mechanism is provided for monitoring the service life of layup molds, such as a mold used for the manufacturing of parts in an autoclave oven. A body that is suitable for use in the autoclave oven is located on the mold. At least one rod is located on the body which elongates and contracts due to heat. At least one gear is located on the body so as to rotate about its own axis and which extends when the heat in the autoclave oven increases to trigger the gear. A gear is triggered by the rod to rotate about its own axis. A counter is triggered with the rotational movement of the gear and provides information about the number of uses of the mold depending on the rotational movement.

10 Claims, 3 Drawing Sheets

(56) References Cited

OTHER PUBLICATIONS

Figure 1:
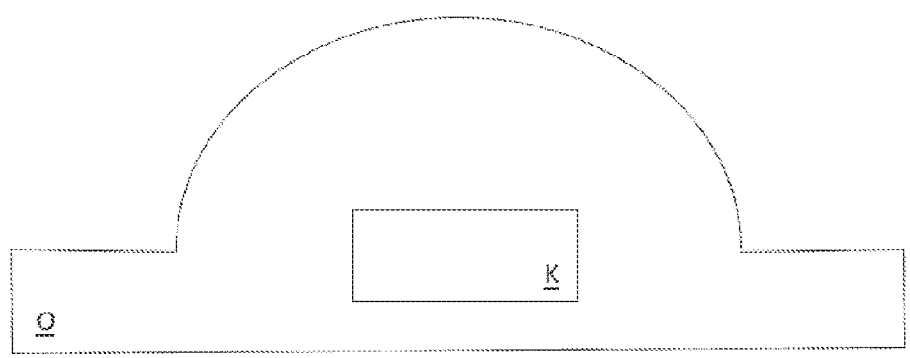

Written Opinion of the International Preliminary Examining Authority for PCT application No. PCT/TR2021/050276, mailed Mar. 23, 2022.
International Preliminary Report on Patentability, completed Jun. 20, 2022.
International Application Status Report received Apr. 20, 2021.
Response to Written Opinion of the International Preliminary Examining Authority for PCT application No. PCT/TR2021/050276, dated May 18, 2022.

CYCLE COUNTER MECHANISM FOR USE IN AN AUTOCLAVE OVEN

This invention relates to a cycle counter mechanism for monitoring the service life of layup molds.

In industrial applications, counters are used for the service life information of composite layup molds. By means of a stationary indicator on the composite layup mold, it is known how many times the composite layup mold is used above a temperature value previously entered into the system by the user.

The service life of composite layup molds are predetermined by their manufacturers. The composite layup mold is replaced when the predetermined number of uses by the operator is reached. However, the life of the composite layup mold does not depend only on the number of uses. The service life of the composite layup mold may vary depending on different factors such as the temperature and/or pressure applied to the mold. The service life determined by the manufacturer may be longer or shorter than the actual service life. In this case, failures may occur in the final part, for example when the composite layup mold completes its service life before the number of uses determined by the manufacturer. Although it is known how many times a composite layup mold is used, abrasions etc. occur in the mold due to different temperatures to which the composite layup mold becomes exposed. In this case too failures may occur in the final product. If the composite layup mold does not complete its service life when the number of uses determined by the manufacturer is reached, in turn, the operating costs may increase when the composite layup mold is replaced.

The United States patent document U.S. Pat. No. 5,452,335, which forms part of the state of the art, describes a counter for monitoring the cycles beyond a temperature value previously entered into the system using temperature-sensitive means.

The United States patent document U.S. Pat. No. 6,629,499B1, which forms part of the state of the art, describes a mechanical timer that operates by using the ambient temperature differences during daytime and nighttime periods. The mechanical timer is operates using ambient temperature differentials.

Another patent document is EP0581400A1, which forms part of the state of the art. EP0581400A1 is describing a display device for the number of heatings performed, particularly for the purpose of autoclave sterilization. The display device can be manufactured in small size, so that it can be easily attached to a semi-disposable surgical instrument for indicating the number of times the instrument has been subjected to high heat.

Another patent document is IT201800006509A1, which forms part of the state of the art. IT201800006509A1 is describing a cycle counter device for use with molds made of composite material configured so that it can be associated with a mold, count the number of cycles to which it is subjected and provide a visual indication thereof.

By virtue of a mechanism developed according to the present invention, a mechanism is developed for determining the number of times a mold for composite layups is used.

A further object of the present invention is to develop a cycle counter mechanism which enables an automatic and controlled execution of the detection of the use of composite layup molds.

Yet a further object of the present invention is to develop a cycle counter mechanism which enables the detection of the use of composite layup molds in a manner that is independent of manpower.

Still a further object of the present invention is to develop a simple, easy-to-use, practical, efficient, productive and reliable cycle counter mechanism.

The cycle counter mechanism, which is realized to achieve the object of the present invention and is defined in the first claim and in the claims depending on this claim, for a mold on which a lay-up process is carried out for the manufacturing of parts to be cured in an autoclave oven, comprises a rod, which is provided on a body suitable for use in the autoclave oven, and is capable to elongate and contact depending on the heat in the setting when it exceeds a reference temperature value previously set by the manufacturer to a system controlling the heat of the autoclave oven, at least one gear provided on the body so as to rotate about its own axis, and a counter which is triggered to provide information about the number of use and/or the remaining service life of the mold as a result of getting triggered by the contact of the elongating rod which elongates with the increasing heat in the autoclave oven so as to provide the gear to rotate about its own axis by contacting a protrusion provided on the gear.

The cycle counter mechanism according to the present invention comprises a body having multiple rods, each triggering the gear at a different time than the other, while the mold is heated in the autoclave oven. It includes a bar, which enables each to show different elastic deformation, manufactured in different lengths and/or diameters, and triggered by coming in different sizes for different temperature values. Thus, the rods are triggered for many temperature values instead of the sole temperature value previously entered into the system by the manufacturer so that the remaining service life of the mold is determined.

In an embodiment of the present invention, the cycle counter mechanism comprises more than one rod, each manufactured from a different material and each having a structure that can elongate as a result of becoming induced by the pressure and/or temperature variation it is exposed to. The number of mold uses may vary due to different temperatures and/or pressures. By means of providing multiple rods with different elongation and/or expansion coefficients in the mechanism, at a temperature below a reference temperature value, the number of uses and/or the service life of the mold is/are monitored with the rods becoming induced at different temperature and/or pressure values.

In an embodiment of the present invention, the cycle counter mechanism comprises a rod manufactured from a bimetallic material. The number of use of the mold may vary due to different temperatures and/or pressures. By means of multiple rods showing different elastic deformation in the mechanism, it is provided to monitor the number of uses of the mold with the rods becoming induced at different temperature and/or pressure values.

In an embodiment of the cycle counter mechanism according to the present invention, the number of uses of the mold may vary due to different temperatures and/or pressures. By manufacturing the rod from a shape memory alloy material, the rod is triggered at different temperature and/or pressure values, providing information on the number of uses and/or service life of the mold.

In an embodiment of the cycle counter mechanism according to the present invention, the rod manufactured from a bimetallic and/or shape memory alloy material, has a structure that elongates by becoming triggered with the variation of pressure and/or temperature it is exposed to. As a result of the size of rods changing due to temperature and/or pressure variation and the gear is driven and meanwhile keeping its size constant, it is provided to carry out a reliable monitoring of the number of use.

In an embodiment of the present invention, the cycle counter mechanism comprises a body that is detachably mounted onto the mold, enables adapting itself to different molds. For different molds that need to be used at different temperatures and/or pressures, the body is placed on the mold and provides adaptation. In this way, the counter mechanism is also used for the temperature and/or pressure values that the layup mold is exposed to, instead of the reference temperature determined by the manufacturer.

In an embodiment of the present invention, the cycle counter mechanism comprises more than one gear so as to adapt to higher cycle numbers rather than limited cycle numbers by virtue of more than one gear on the body, each of which can trigger the other, and more than one gear, each of which can trigger a different gear. In this way, the number of uses and/or service life information can be monitored on the counter for higher number of cycles by rotating each other.

In an embodiment of the present invention, the cycle counter mechanism comprises a counter that can be used for the same and/or different molds, enabling a recount to be made by getting reset by the user and/or getting reduced to a value predetermined by the user. Thus, it can be used in other layup molds by removing it from the layup molds that have expired their service life and/or will be sent to maintenance. The counter is provided to make further cycle counting by resetting it and/or reducing it to the reference value.

In an embodiment of the present invention, the cycle counter mechanism comprises an additional tracking indicator for molds in order for the maintenance and/or repair operations predetermined by the manufacturer to be monitored. In this way, it is ensured that molds that are due for maintenance and/or repair are monitored simultaneously.

In an embodiment of the present invention, the cycle counter mechanism provides the monitoring of the number of uses of the mold to be made through the gear without the need for an additional mechanism by virtue of the counter that is positioned on the gear.

In an embodiment of the present invention, the cycle counter mechanism is suitable for use in autoclaves under high temperature and/or pressure for curing the final parts of aerospace vehicles. It is ensured that the number of uses of the mold is monitored thanks to the use of counter when manufacturing the final parts under very high temperatures and/or pressures.

The cycle counter mechanism realized to achieve the object of the present invention is shown in the accompanying figures, among which;

FIG. 1—is a schematic view of the autoclave and composite mold.

Figure 2:
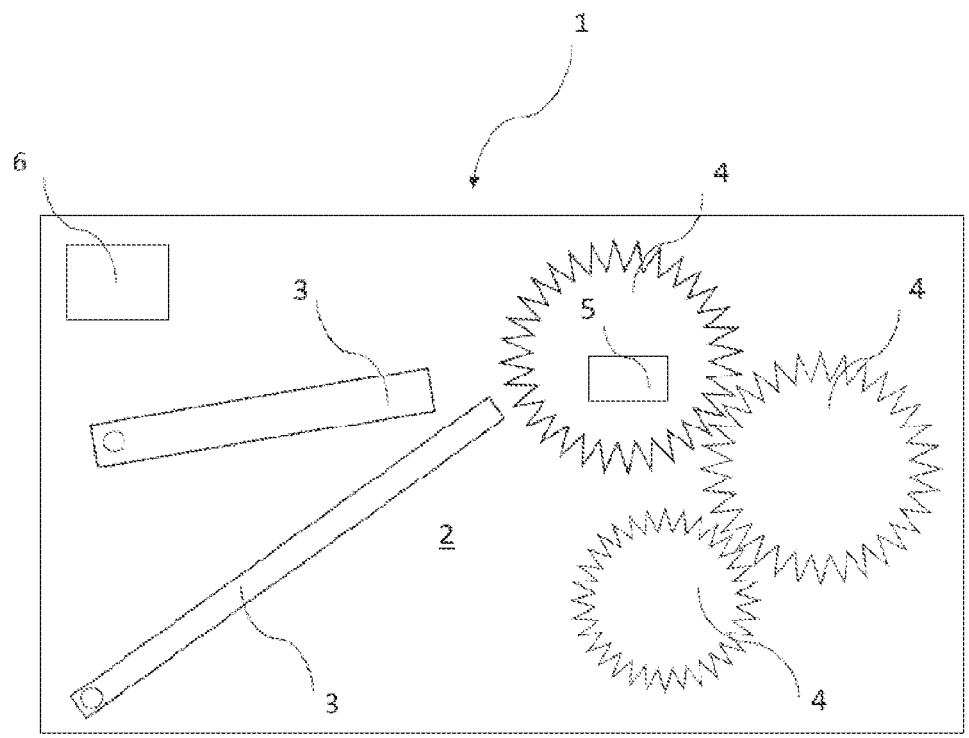

FIG. 2—is a schematic view of the cycle counter mechanism.

Figure 3:
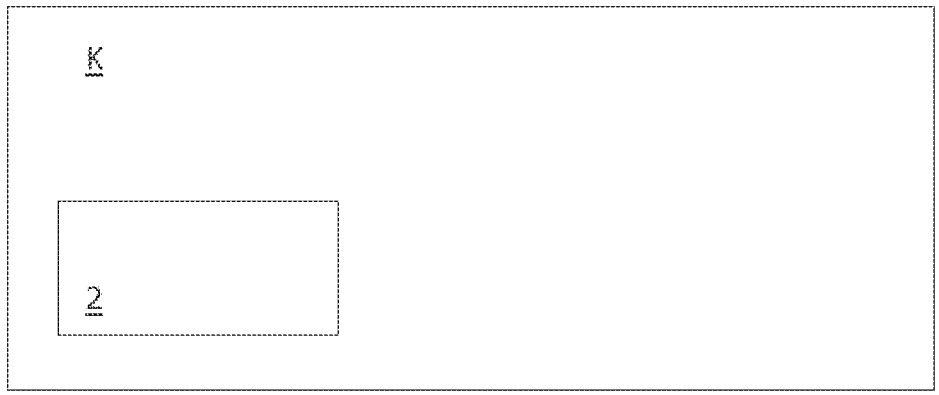

FIG. 3—is a schematic view of the mold and cycle counter mechanism.

Figure 4:
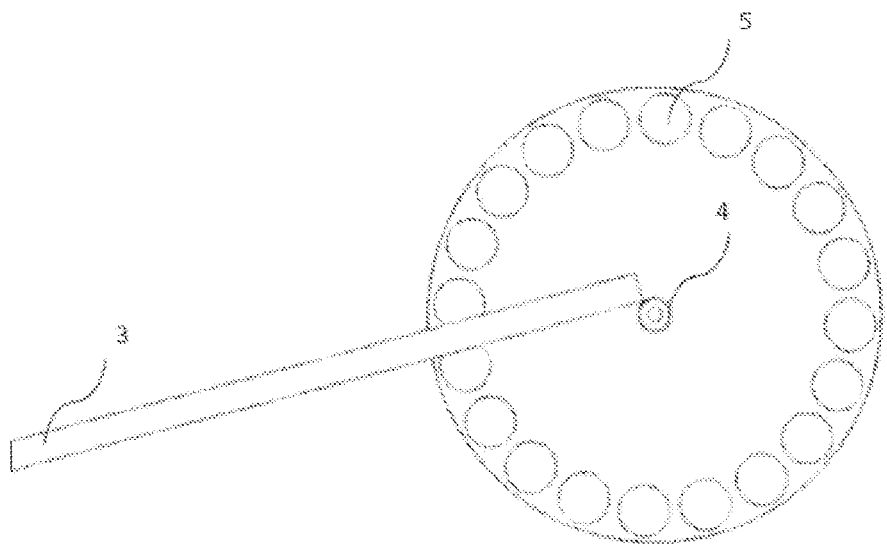

FIG. 4—is a schematic view of the cycle counter mechanism.

Figure 5:
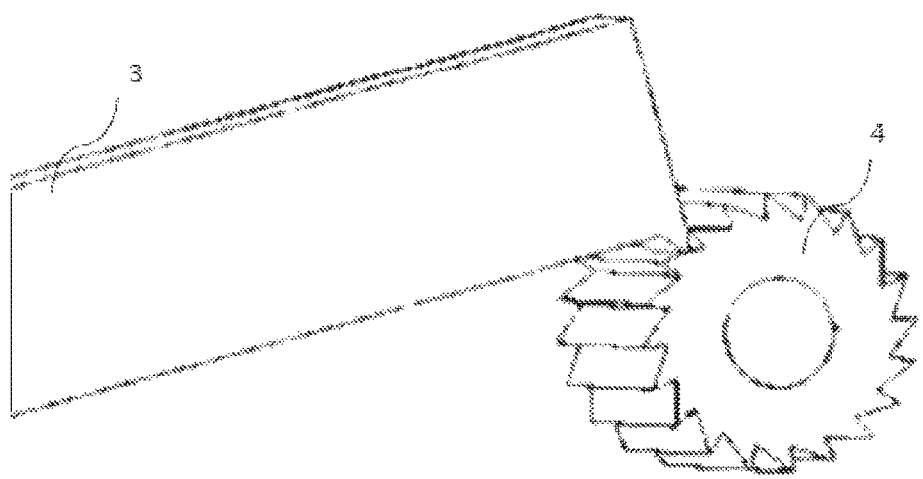

FIG. 5—is a schematic view of the cycle counter mechanism.

The parts in the figures are individually numbered and the equivalents of these numbers are given below.
1. Cycle counter mechanism
2. Body
3. Rod
4. Gear
5. Counter
6. Tracking indicator
   (K) Mold
   (O) Autoclave oven The cycle counter mechanism (1) comprises at least one mold (K) used for the production of parts in the autoclave oven (O), a body (2) suitable for use in the autoclave oven (O) and located on the mold (K), at least one rod (3) which is located on the body (2) and is capable of elongating and contacting due to heat, at least one gear (4) located on the body (2) so as to rotate about its own axis, a gear (4) which extends when the heat in the autoclave oven (O) increases and triggers the gear (4), and which is triggered by the rod (3) to rotate about its own axis, and a counter (5) which is triggered with the rotational movement of the gear (4) and provides information about the number of uses of the mold (K) depending on the rotational movement. (FIG. 1 and FIG. 2)

The cycle counter mechanism (1) according to the present invention comprises a body (2) having multiple rods, each triggering the gear (4) at a different time than the other while the mold (K) is heated in the autoclave oven (O). (FIG. 2)

The cycle counter mechanism (1) comprises at least one mold (K) used for the production of parts in the autoclave oven (O), and a body (2) which is located on the mold (K) and is suitable for use in the autoclave oven (O). At least one gear (4) located on the body (2) so as to rotate about its own axis by means of at least one rod (3) which is located on the body (2) and is capable to elongate and contract due to heat, extends and triggers the gear (4) when the heat in the autoclave oven (O) increases. The gear (4), which is triggered by the rod (3) and rotates about its own axis, comprises a counter that is triggered by the gear's (4) rotational movement and gives information about the number of uses of the mold (K) depending on the rotational movement.

By virtue of multiple rods (3) located on the body (2), the cycle counter mechanism (1) provides the triggering of the gear (4) with each of the rods triggering it at a different time than the other while the mold (K) is heated in the autoclave oven (O).

In an embodiment of the present invention, the cycle counter mechanism (1) comprises more than one rod (3), each manufactured from a different material. By virtue of multiple rods (3) for different temperature and/or pressure values, the number of uses and/or service life of the mold (K) is monitored.

In an embodiment of the present invention, the cycle counter mechanism (1) comprises a rod (3) manufactured from a bimetallic material. It comprises more than one rod (3) manufactured from a bimetallic material and elongating as a result of getting triggered by the pressure and/or temperature variation it is exposed to. As a result of producing the rod (3) from a bimetallic material, the rod (3) can restore itself when the influence of temperature and/or pressure passes away.

In an embodiment of the present invention, the cycle counter mechanism (1) comprises a rod (3) manufactured from a shape memory alloy material. It comprises more than one rod (3) manufactured from a shape memory alloy material and elongating as a result of becoming triggered by the pressure and/or temperature variation it is exposed to. As a result of producing the rod (3) from a shape memory alloy material, the rod (3) can restore itself when the influence of temperature and/or pressure passes away.

In an embodiment of the present invention, the cycle counter mechanism (1) comprises a gear (4) of which the shape and/or size remains constant during the manufacturing of parts in the autoclave oven (O). As a result of manufacturing the rod (3) from a bimetallic and/or shape memory alloy material, it is triggered under the influence of temperature and/or pressure. The gear (4) manufactured from a material which is not affected by temperature and/or pressure values is ensured to remain in its fixed form for the rod (3) which is triggered under the influence of temperature and/or pressure.

In an embodiment of the present invention, the cycle counter mechanism (1) comprises a body (2) detachably mounted onto the mold (K), enables adapting itself to different molds (K). It can be used for molds (K) which are exposed to different temperature and/or pressure influences.

In an embodiment of the present invention, the cycle counter mechanism (1) comprises more than one gear (4) located on the body (2) so that each of which can trigger the other, and more than one rod (3) located on the body (2) so that each of which can trigger a different gear (4). It can be used for higher number of uses by virtue of multiple gears (4) that actuate each other and/or of multiple rods (3) each of which actuating a different gear (4).

In an embodiment of the present invention, the cycle counter mechanism (1) comprises a counter (5) that can be used for the same and/or different molds (K) and that enables recounts to be made by getting reset by the user and/or getting reduced to a predetermined value by the user. In this way, the cycle counter mechanism (1) is used even if the mold (K) is not used.

In an embodiment of the present invention, the cycle counter mechanism (1) comprises at least one tracking indicator (6) on which the service life information of the mold (K) predetermined by the manufacturer is provided and which is located on the body (2) for tracking the maintenance and/or repair of the mold (K). In this way, it is ensured that molds (K) that are due for maintenance and/or repair are monitored simultaneously for maintenance and/or repair.

In an embodiment of the present invention, the cycle counter mechanism (1) comprises a counter (5) positioned on the gear (4). By virtue of the counter (5) positioned on the gear (4), the number of uses of the mold is monitored on the gear (4).

In an embodiment of the present invention, the cycle counter mechanism (1) comprises a body (2) suitable for use in the production of composite parts in aerospace vehicles. In aerospace vehicles manufactured at high temperatures and/or high pressures, the number of uses of the mold (K) for the production of composite parts is hereby monitored.

The invention claimed is:

1. A cycle counter mechanism (1) comprising:
   at least one mold (K) used for production of parts in an autoclave oven (O),
   a body (2) suitable for use in the autoclave oven (O) and located on the mold (K),
   a plurality of rods (3) located on the body (2), each of which elongates and contracts, due to heat,
   a plurality of gears (4) located on the body (2) that each rotate about an associated axis and when the heat increases in the autoclave oven (O), each of the plurality of rods (3) extends and triggers an associated one of the plurality of gears (4) to rotate about the axis associated with that gear,
   a counter (5) which is triggered with a rotational movement of the at least one of the plurality of gears (4) and provides information about a number of uses of the mold (K) depending on the rotational movement, and
   wherein each of the plurality of rods (3) triggers each associated gear of the plurality of gears (4) at a different time while the mold (K) is heated within the autoclave oven (O).

2. The cycle counter mechanism (1) according to claim 1, wherein each of the plurality of rods (3) is manufactured from a different material.

3. The cycle counter mechanism (1) according to claim 1, wherein at least one of the plurality of rods (3) is manufactured from a bimetallic material.

4. A cycle counter mechanism (1) according to claim 1, wherein at least one of the plurality of rods (3) is manufactured from a shape memory alloy material.

5. The cycle counter mechanism (1) according to claim 1, wherein each of the plurality of gears (4) has a shape and/or size which remains fixed during the production of parts in the autoclave oven (O).

6. The cycle counter mechanism (1) according to claim 1, wherein the body (2) is detachably mounted onto the mold (K).

7. The cycle counter mechanism (1) according to claim 1, wherein the counter (5) is adapted for use for a same and/or different mold (K) and enables recounts to be made by getting reset by a user and/or getting reduced to a predetermined value by the user.

8. The cycle counter mechanism (1) according to claim 1, comprising at least one tracking indicator (6) on which service life information of the mold (K) predetermined by a manufacturer thereof is provided and which is located on the body (2) for tracking maintenance and/or repair of the mold (K).

9. The cycle counter mechanism (1) according to claim 1, wherein the counter (5) is positioned on one of the plurality of gears (4).

10. The cycle counter mechanism (1) according to claim 1, wherein the body (2) is adapted for use in production of composite parts for aerospace vehicles.

* * * * *